(12) United States Patent
Gimson

(10) Patent No.: US 6,889,559 B2
(45) Date of Patent: May 10, 2005

(54) FLOW METERING

(75) Inventor: Chris Gimson, Bolton (GB)

(73) Assignee: Endress + Hauser Limited, Manchester (GB)

( * ) Notice: Subject to any disclaimer, the term of this patent is extended or adjusted under 35 U.S.C. 154(b) by 0 days.

(21) Appl. No.: 10/475,850

(22) PCT Filed: Apr. 26, 2002

(86) PCT No.: PCT/EP02/04637
§ 371 (c)(1),
(2), (4) Date: Oct. 31, 2003

(87) PCT Pub. No.: WO02/090897
PCT Pub. Date: Nov. 14, 2002

(65) Prior Publication Data
US 2004/0149027 A1 Aug. 5, 2004

(30) Foreign Application Priority Data
May 3, 2001 (GB) ............................................. 0110961

(51) Int. Cl.⁷ ................................................. G01F 1/00
(52) U.S. Cl. ....................................................... 73/861
(58) Field of Search ............................. 73/861, 861.24, 73/861.52, 756, 866.5; 429/24; 492/22

(56) References Cited

U.S. PATENT DOCUMENTS

| 1,960,568 | A | | 5/1934 | Abrams |
| 4,074,571 | A | | 2/1978 | Burgess |
| 4,171,643 | A | * | 10/1979 | Frick ........................ 73/861.24 |
| 4,862,744 | A | | 9/1989 | Zorb et al. |
| 5,339,687 | A | | 8/1994 | Gimson et al. |
| 5,780,735 | A | | 7/1998 | Kadohiro et al. |
| 6,395,415 | B1 | * | 5/2002 | Hoehn et al. .................. 429/22 |
| 6,672,173 | B2 | * | 1/2004 | Bell ......................... 73/861.52 |

FOREIGN PATENT DOCUMENTS

| DE | 196 09 823 A1 | 9/1997 |
| EP | 1 227 326 A2 | 7/2002 |

* cited by examiner

Primary Examiner—Edward Lefkowitz
Assistant Examiner—Jewel V. Thompson
(74) Attorney, Agent, or Firm—Bacon & Thomas

(57) ABSTRACT

A flow meter incorporating thermal loss sensors and an installation adapter to provide known flow conditions upstream of the meter. The installation adapter is in the form of a tubular extension projecting from a flange which in use is sandwiched between a pipeline flange and a flow meter flange. The flanges are configured such that a passageway defined by the adapter extension is located in a predetermined position relative to the flow meter. The flow meter may comprise a sensor array supporting at least three sensors which are not in alignment, one of those sensors being located centrally within the flow meter and the others being distributed at equal distances around the central position. In use, normal readings may be taken from a single one of the sensors, the other sensors being used for initial calibration and subsequent calibration test purposes only. A comparison is made between the relative values of the outputs of the different sensors to identify sensor drift or potentially significant changes in flow conditions.

11 Claims, 5 Drawing Sheets

FLOW METERING

This application is a 371 of PCT/EPO02/04637 Apr. 26, 2002.

FIELD OF THE INVENTION

The present invention relates to flow metering, and in particular to a flow meter installation adapter, a flow sensor array, and a method for operating a multi-sensor thermal loss flow meter.

BACKGROUND OF THE INVENTION

Flow meters are well known devices that can be used to measure the rate of flow of a fluid such as a liquid or gas through a pipe. Known flow meters monitor various conditions such as the rate of loss of heat from a heated sensor or differential pressures to provide an output representative of flow conditions within the body of a flow meter. Each type of known flow meter has its advantages and disadvantages but with many flow meters and in particular thermal loss flow meters it is difficult to pre-calibrate a meter without a precise knowledge of the operational environment in which that meter is to be fitted. As a result, it is often the case that flow meters are delivered to the end user on the basis that after installation they will be adjusted such that the flow meter output does represent a true measure of the flow through the meter. Such an approach requires highly skilled technicians to install meters and it would clearly be highly desirable to rely upon factory-calibration to a much greater extent than is possible at present.

One problem encountered when installing flow meters is that such meters are generally inserted between flanges of a pipeline. Thus the flow meter will define an inlet of factory-determined dimensions which in use is located downstream of a passageway defined by a pipe of unknown dimensions. Even if for a particular installation the nominal internal diameter of a pipe upstream of the intended meter location is known, there is almost inevitably a discontinuity as between the meter body inlet and the pipe immediately upstream of that inlet which generates unpredictable effects within the meter body. Such unpredictable effects make it impossible reliably to calibrate a flow meter until that flow meter has been installed in its final place of use.

SUMMARY OF THE INVENTION

It is an object of the present invention to obviate or mitigate the problem outlined above.

According to the present invention, there is provided a meter installation adapter for fitting upstream of a flow meter in a fluid-conveying pipeline, the flow meter in use being positioned downstream of a flange defined by the pipeline, wherein the adapter comprises a tubular extension having an outside diameter sized to enable its insertion into the pipeline upstream of the pipeline flange, and the adapter has a downstream end configured to engage the flow meter such that a passageway defined by the adapter extension is located in a predetermined orientation relative to the flow meter.

Thus, regardless of the internal diameter or condition of the upstream pipeline, the adapter extension provides the flow meter with known upstream conditions. The internal surface of the pipeline immediately upstream of the flow meter is masked by the adapter extension. In addition, the adapter extension prevents any gasket used to seal the flow meter to the pipeline flange from protruding into the flow passageway immediately upstream of the meter.

The tubular extension may itself be mounted on a flange which in use is inserted between a flange of the flow meter and the pipeline flange. A factory-defined seal may be provided between the flow meter and the adapter flange, obviating the need to provide a gasket of unpredictable configuration between the installation adapter and the flow meter.

A meter installation adapter as defined above does make it possible to predetermine conditions immediately upstream of a flow meter and thereby to improve the accuracy of factory calibration of a flow meter. The conditions in which the flow meter is used can however change in an unpredictable manner as a result of other factors, for example instability in the flow resulting from upstream bends and discontinuities in the pipeline, particularly when flow rates vary to a substantial extent. For example, if a thermal loss flow meter provided with a single thermal loss sensor is calibrated on the basis that a fully developed flow is expected in the vicinity of the sensor, and yet conditions change such that the fully developed flow is disrupted, the relationship between the sensor output and the flow may be radically altered, rendering the meter output inaccurate. If a single sensor is positioned at three quarters of the radius of the pipeline away from the pipeline axis in a position which can be represented at 12 o'clock, the same sensor located at the same distance from the pipeline axis at a position which could be represented as for example 3 o'clock could produce a very different output if the flow meter is positioned downstream of a disturbance creator such as a single bend in one plane or more complex bend combinations. Where a flow meter is positioned other than in a fully developed flow a change in flow rate can in effect cause a rotation in the flow conditions in the vicinity of the flow meter. A flow meter calibrated in one set of conditions therefore may provide inaccurate data if those conditions change.

It is known to manufacture a flow meter in which wires extend across the passage through which flow is to be monitored, sensors being located at intersections of the wires. Such an arrangement gives a good distribution of sensing points within the passageway, enabling the user to generate a flow representing output based on the combination of outputs from the different sensors. Such an arrangement is however difficult to install and maintain.

It is also an object of the present invention to obviate or mitigate the problems outlined above with regard to flow sensing structures.

Thus, according to a second aspect of the present invention, there is provided a sensor array for positioning in a passageway through which fluid flow is to monitored, comprising a unitary support extending from one wall of the passageway and extending at least partially around a central portion of the passageway, and at least three flow sensors mounted on the support in a non-linear array. By mounting three or more sensors on an annular or similarly shaped structure sensors capable of detecting asymmetry in flow can be provided in a simple and robust structure. Preferably that structure also supports a sensor located centrally within the passageway.

Thermal loss flow meters have certain advantages and as a result have been installed in a wide range of applications. Such flow meters do however have the disadvantage that energy is inevitably dissipated given that the flow meters operate on the basis that energy is lost into the flow at a rate related to that flow. In systems where multiple sensors are required to detect asymmetric flow patterns the energy losses from the multiple sensors can become significant, particularly in pipeline networks where many flow meters are required.

It is an object of the present invention to obviate or mitigate the disadvantages in terms of energy loss referred to above.

Thus, according to a third aspect of the present invention there is provided a method for operating a flow meter comprising a plurality of thermal loss sensors distributed about a passageway through which flow is to be monitored, wherein during normal operation a single sensor is energized to provide an output representative of thermal loss due to the now adjacent that sensor, and an output representative of flow rate is derived from the output representative of thermal loss on the basis of a predetermined calibration relationship between flow rate and thermal loss from that single sensor, the calibration relationship being established on the basis of outputs derived from all of the sensors at calibration, a representation of the relative values of the outputs of the sensors at calibration being recorded, and during use the accuracy of the calibration being tested by energizing all of the sensors and comparing the relative values of the resultant sensor outputs with the recorded relative values, changes in the relative values as between calibration and test being indicative of loss of calibration accuracy.

Given that in normal use for most of the time only one sensor is energised thermal losses are not substantially increased as compared with a system incorporating only a single thermal loss sensor. Periodic testing however by energising all of the sensors and comparing the resultant outputs with pre-recorded outputs enables loss of calibration accuracy to be detected.

Embodiments of the present invention will now be described, by way of example, with reference to the accompanying drawings, in which:

DESCRIPTION OF THE PREFERRED EMBODIMENTS

Figure 1:
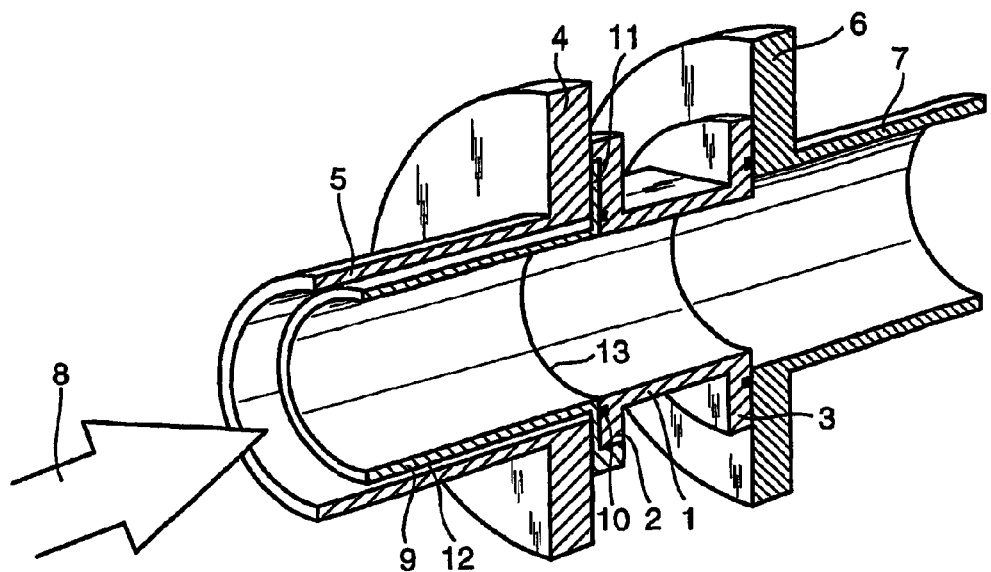
FIG. 1 is a sectioned perspective view of a flow meter body mounted between two flanges of a pipeline and downstream of a meter installation adapter in accordance with the present invention.
Figure 2:
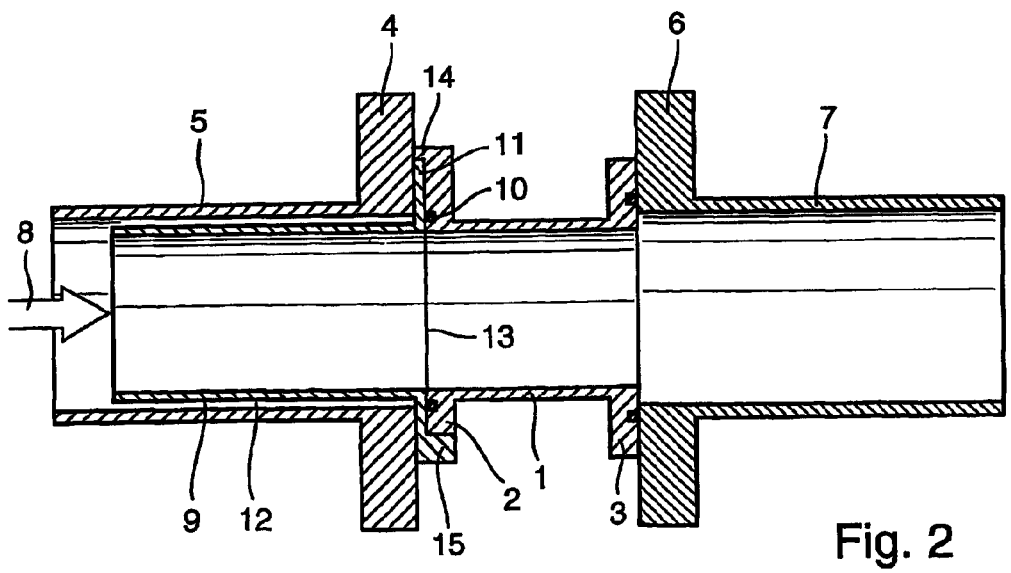
FIG. 2 is a sectional view through the assembly of FIG. 1.

Referring to FIGS. 1 and 2, the illustrated assembly comprises a flow meter body 1 defining flanges 2 and 3 sandwiched between a flange 4 mounted on one end of a pipeline 5 and a flange 6 mounted on one end of a pipeline 7. In use, a flow meter sensor (not shown) is supported in the flow meter body 1 so as to be exposed to fluid flowing in the direction of arrow 8 through the assembly. A meter installation adapter 9 extends into the upstream pipe 5 from the body 1. The adapter is sealed to the meter flange 2 by an O-ring 10 that seats against a flange 11 on the downstream end of the adapter 9. The outside diameter of the adapter 9 is less than the inside diameter of the pipe section 5 such that an annular space 12 is defined outside the adapter 9. The inside diameter of the adapter 9 is the same as the inside diameter of the meter housing 1 and the flanges 2 and 11 are dimensioned such that the axes of the body 1 and adapter 9 are in alignment. Thus there is no surface discontinuity at the interface between the adapter 9 and the body 1 represented by line 13.

As best seen in FIG. 2, the flange 2 supports a lip 14 which projects over the edge of the flange 11 from which the adapter 9 extends. The flange 2 remote from the lip 14 also defines a recess to receive a projecting portion 15 extending in the axial direction from the flange 11. This ensures that the installer can ensure that the extension 9 is correctly aligned with the body 1. In the illustrated case, the axial length of the extension 9 is greater than the spacing between the flanges 4 and 6. Such an arrangement could only be installed if at the time of installation the spacing between the flanges 4 and 6 can be increased to at least the axial length of the adapter 9. Without any movement of the flanges 4 and 6 however the flow meter body 1 can be slipped out from the gap between the flanges 4 and 6 without having to displace the adapter 9. Although clearly it is desirable for the adapter extension 9 to be as long as possible, even the use of a very short adapter extension enhances the predictability of conditions within the flow meter. For example, an extension only a few millimeters long would be sufficient to remove unpredictable conditions immediately adjacent the interface between the pipeline flange and the flow meter flange. For example such a short extension would prevent a sealing gasket protruding across the inlet end of the flow meter.

Figure 3:
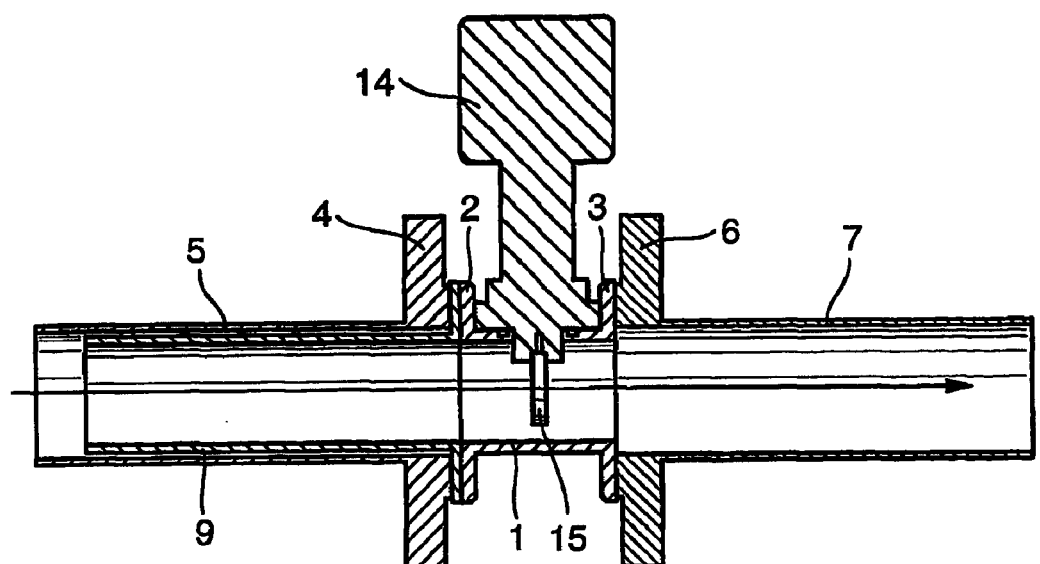
FIG. 3 is a view similar to that of FIG. 2 but showing a thermal loss flow meter sensor support structure mounted in the body of the flow meter shown in FIG. 2.
Figure 4:
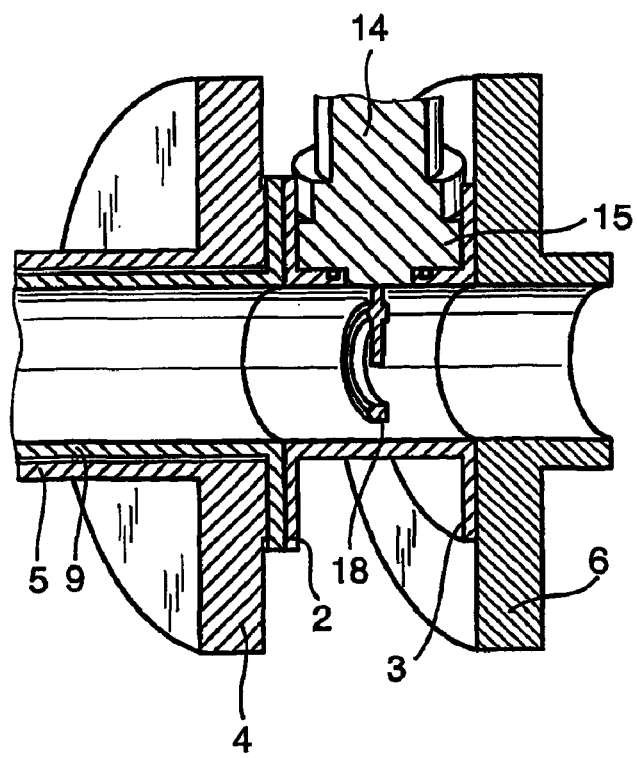
FIG. 4 is a perspective sectional view through the assembly of FIG. 3.
Figure 5:
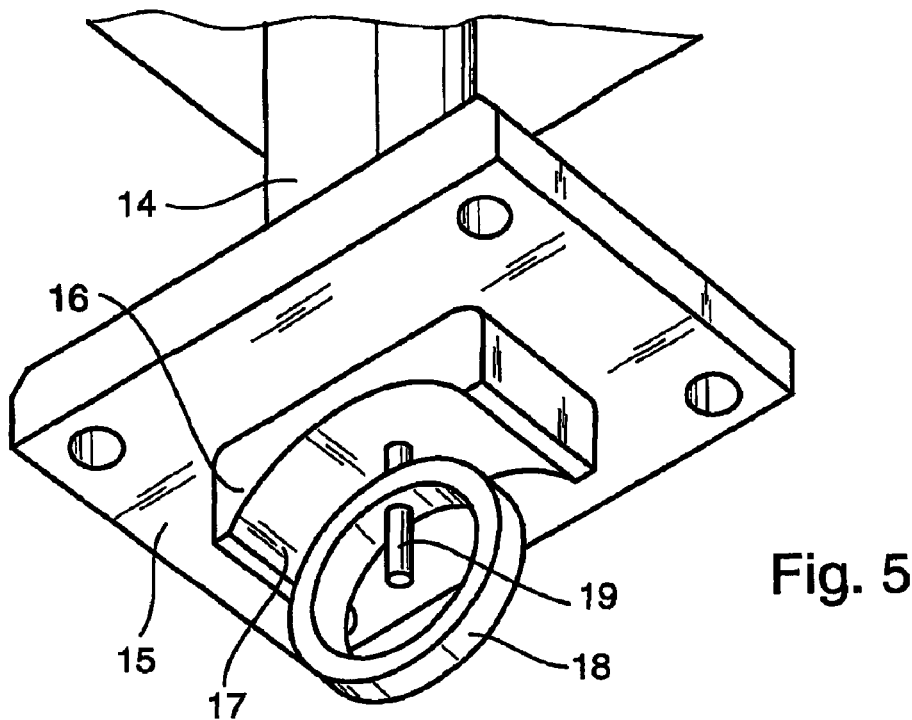
FIG. 5 is a view from below of the sensor support structure shown in FIG. 4.
Figure 6:
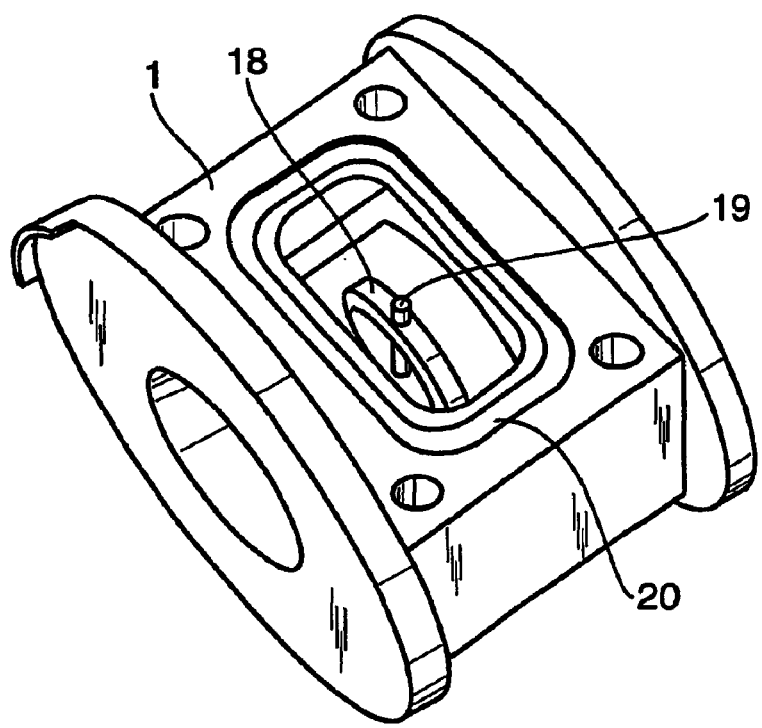
FIG. 6 is a view from above showing details of the flow meter housing and the orientation in use of the sensor support structure within that housing.

FIGS. 3 and 4 show the assembly of FIGS. 1 and 2 after a flow meter has been mounted on a side of the flow meter body 1 not shown in FIGS. 1 and 2. The flow meter comprises a housing 14 extending upwards from a base plate 15. As best shown in FIGS. 5 and 6, the base plate 15 supports a projection 16 defining an arcuate inner surface 17 which is a continuation of the inner surface of the body 1. A ring sensor 18 is supported on a radial rod 19 extending out of the surface 17. The body 1 defines a groove 20 which in use receives a sealing ring (not shown), the plate 15 being secured onto the body by four bolts (not shown) extending through the apertures shown in FIGS. 5 and 6.

The ring 18 supports four sensors (not shown) spaced at 90° intervals around the ring. The rod 19 also supports a sensor (not shown) adjacent its end. In use, the sensor supported by the rod 19 is located on the axis of the passageway defined through the body 1 and each of the sensors supported by the ring 18 is located at a distance from the passageway axis equal to three quarters of the radius of the passageway.

Referring to FIGS. 3 and 4, given that there is no discontinuity between the inner surface of the adapter 9 and the inner surface of the body 1, flow conditions upstream of the sensor ring 18 are determined largely by the characteristics of the adapter rather than the characteristics of the pipe 5 into which the adapter 9 has been inserted. Therefore the meter can be calibrated in the factory on the basis that conditions upstream of the meter are known. If the adapter 9 was not present, there would be a discontinuity as between the opening defined by the meter body. 1 and the inner diameter of the pipe 5. Furthermore, if a gasket was used to form a seal between the meter body 1 and the pipe flange 4, the gasket might well project radially inwards on at least one side so as to partially obstruct the inlet end of the meter body 1. The use of the adapter in accordance with the present invention therefore ensures that conditions upstream of the meter are known with certainty as far as the upstream end of the adapter.

The sensor support structure shown in FIGS. 3 to 6 provides a robust structure which is easy to mount within the flow meter, does not present an unduly large obstruction to flow through the meter, and yet makes it possible to monitor conditions at four positions spaced around the axis and on the axis itself. As a result a very accurate representation of flow conditions within the flow meter can be obtained. The dimensions of the sensor support structure are such however that a relatively large opening is required as shown in FIG. 6 to enable the insertion and removal of the structure into the flow meter body. An alternative arrangement which does not require such a large opening as illustrated in FIGS. 7 to 10.

Figure 7:
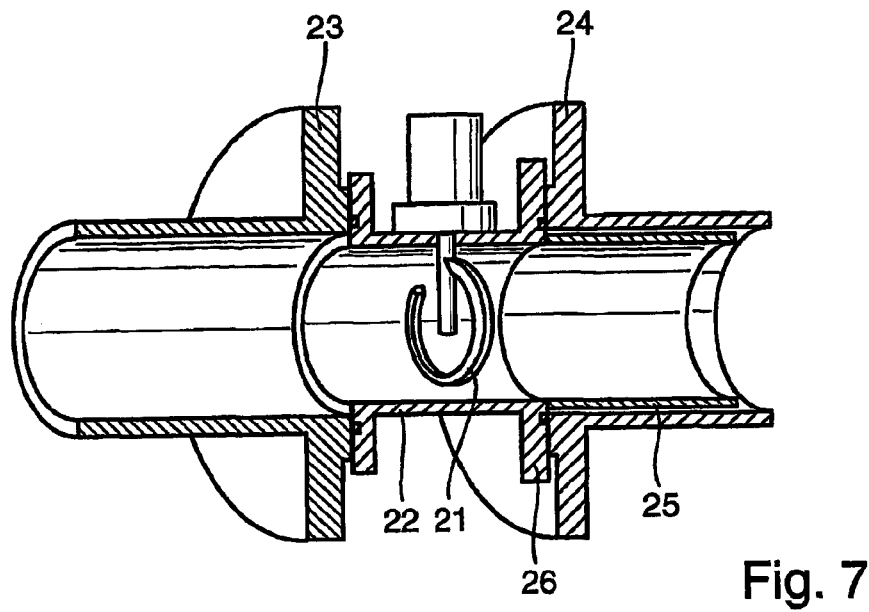
FIG. 7 is a perspective sectional view through an alternative embodiment of the present invention incorporating an alternative sensor support structure.

Referring to FIG. 7, a support structure 21 is mounted in a flow meter body 22 sandwiched between flanges 23 and 24 of a pipeline. A meter installation adapter 25 is fitted upstream of the body 22. As in the case of the embodiment of FIGS. 1 to 6, the adapter is accurately located relative to the body 22 by virtue of the co-operation of formations provided on the body and adapter flanges. In particular, FIG. 7 shows a portion 26 projecting from the adapter flange as it is engaged in a radial slot in the periphery of the body flange. The support structure 21 differs from that shown in FIGS. 3 to 6 however in that rather than being circular it is only part circular so as to define what may be loosely described as a J-shape. Such an arrangement can be manoeuvred into position through a much smaller opening in the body 22 than is required to receive the full ring sensor structure as shown in for example FIG. 5.

Figure 8:
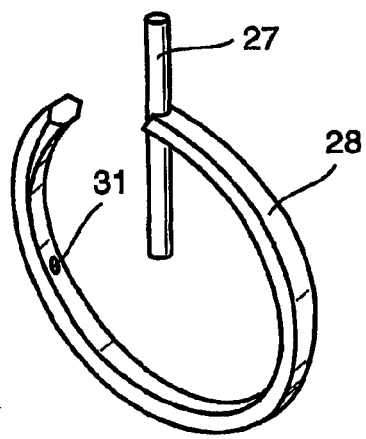
FIG. 8 is a detailed view of the sensor support structure of FIG. 7.
Figure 9:
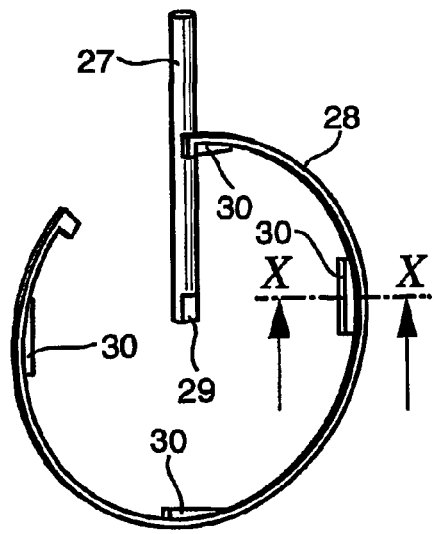
FIG. 9 is a cross section through the sensor support structure of FIG. 8 showing the positioning of sensors within that structure.
Figure 10:
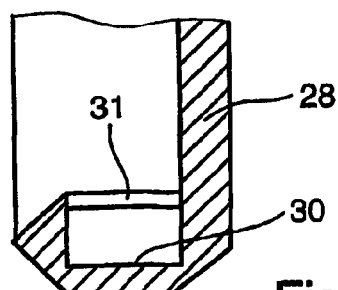
FIG. 10 is a section on the line 10—10 through the structure of FIG. 9.

FIGS. 8, 9 and 10 illustrate in greater detail the form of the sensor support structure 21 of FIG. 7. The structure comprises a radially extending hollow rod 27 and a part-annular portion 28 which is also hollow. A sensor 29 is located in the closed end of the rod 27 and four sensors 30 are supported inside the part-annular portion 28. The sensors 30 are received in an inwardly facing slot formed in the part-annular portion 28 and a metal shim 31 is used to close the slot and protect the sensors 30. The overall assembly is lightweight and the sensors are in good thermal contact through the structure with the surrounding fluid flow. Given the disposition of the total of five sensors, outputs from those five sensors can be used to derive an accurate representation of flow conditions around the structure. Conventional techniques can be used to relate heat loss from the sensors 29 and 30 to local flow conditions. Such conventional techniques may be as described in for example European Patent No. 460044 entitled "Thermal Mass Flow Meter", proprietor Endress+Hauser Limited.

The arrangement of FIGS. 7 to 10 includes five sensors. A three sensor array could be supported on a structure which could be threaded through a relatively small aperture and yet would still be able to sense conditions on the meter axis and at points offset by 90° about the axis. One such structure would have a radially inwardly extending position, an arcuate portion extending around 90° of the passageway, and a further radially inwards portion extending to the passageway axes, sensors being located on the axis and at each end of the arcuate portion.

With an arrangement such as that shown in FIGS. 7 to 10, if each of the thermal sensors 29 and 30 is continuously energised so as to continuously monitor thermal losses to the adjacent flow, the energy consumed will be five times that associated with a conventional single sensor thermal flow meter array. Such losses could be significant in certain applications, particularly where many flow measurements must be taken. The present invention makes it possible to minimise such thermal losses by using all five sensors to calibrate the meter and at intervals to test the accuracy of calibration but relying upon only a single sensor for routine flow measurement purposes.

For example, when the flow meter is initially calibrated measurements will be taken from all five sensors for each of a representative set of calibration flow rates such that the output of each sensor at a particular flow rate is determined. It may be that the outputs from different sensors differ from each other as a result of for example an asymmetry in the flow around the sensor structure. A relationship can nevertheless be derived as between the output of one of the sensors, for example the sensor 30 closest to the free end of the part-annular portion of the structure, and the total mass flow. The relationship between the output of that sensor and the other sensors can be recorded however so that if at some time in the future flow conditions change that change can be detected by a review of the relative values of the outputs of all the sensors. For example, if the flow meter is calibrated on the basis of a fully developed flow such that the outputs of all four of the sensors 30 are identical, the output from any one of those four sensors could be taken to provide the basic measurement value. Periodically the outputs from the four sensors 30 could be compared and, if those outputs were no longer the same this would indicate a need to re-calibrate as either one of the sensors is malfunctioning or flow conditions have changed from those used at the time of calibration from a fully developed flow to a flow in which conditions adjacent different sensors 30 are no longer the same.

Initial calibration could be conducted in the factory. The accuracy of the calibration could then be checked on installation of the meter and its intended site of use, differences between the sensor outputs being taken as an indication that the calibration had to be checked. Similarly, after meter installation the accuracy of the calibration could be checked at periodic intervals so as to detect longer term drifts or loss of calibration accuracy as the result of for example changes in the flow conditions immediately upstream of the meter. This facility can be achieved at minimal extra cost in terms of energy given that except for relatively short test periods only one of the sensors is energised.

Figure 11:
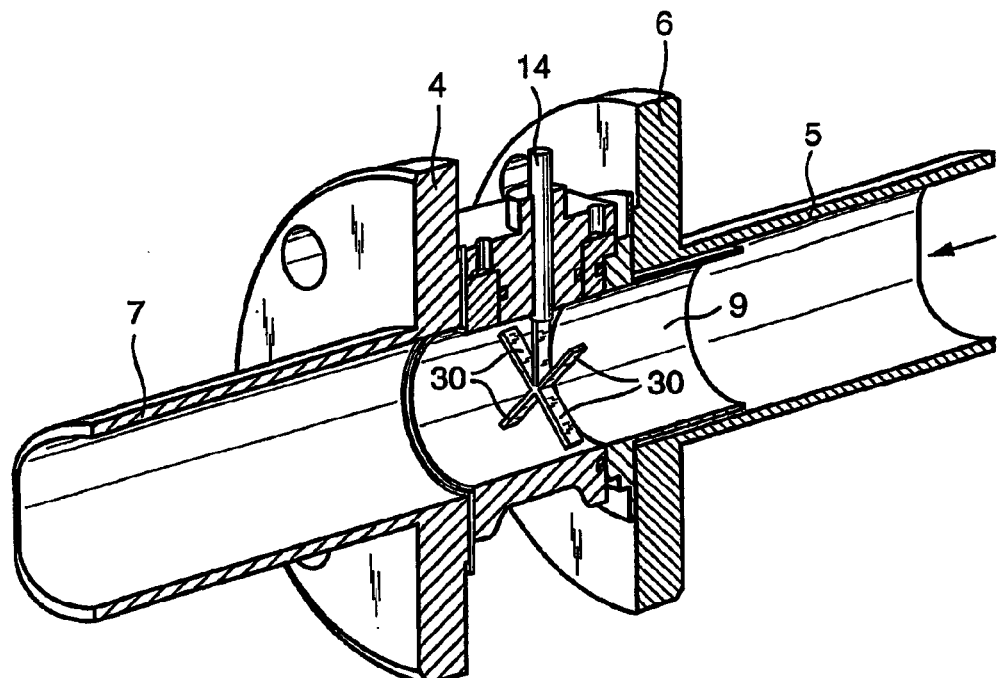
FIG. 11 is a perspective sectional view through a second alternative embodiment of the present invention incorporating a star-like sensor support structure.
Figure 12:
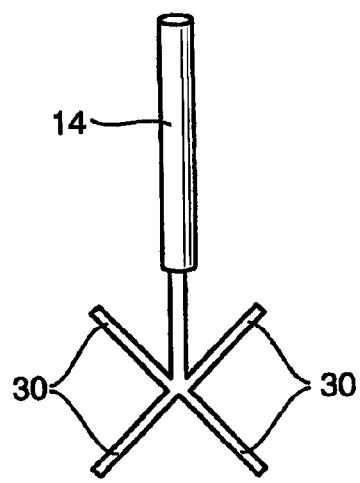
FIG. 12 is a side view of the sensor support structure of FIG. 11.
Figure 13:
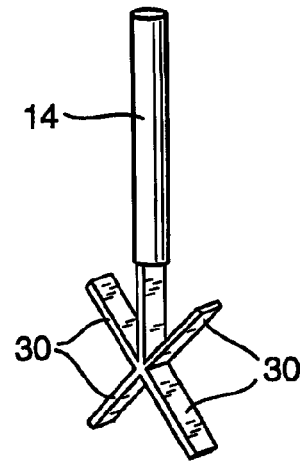
FIG. 13 is a perspective view of the sensor support structure of FIG. 11.

FIG. 11 is a perspective sectional view through a second alternative embodiment of the present invention. According to this preferred embodiment of the inventive sensor the sensor support has a star-like structure. Different views of the sensor support structure of FIG. 11 are shown in FIG. 12 and FIG. 13. The star configuration provides a 'balanced' mounting arrangement for each of the flow sensing elements. This arrangement allows a more balanced distribution of the overall electrical power to the element network with similar performance from each sensor element. That means the performance differences between each individual sensor element (time response, stray body heat losses, power required to each element) are less than with regard to the non symmetrical arrangement of the sensor elements in the before described circular design of the sensor support. According to a preferred embodiment the sensor elements 30 are arranged to the sensor support as shown in FIGS. 12 and 13. It is also possible to attach the sensor elements 30 to the sensor support in a different arrangement.

It is a further advantage of the star-like structure of the sensor support means that the sensor can be manufactured potentially cheaper and easier. The new design allows a set of modular components to be created. Therefore it is quite simple to manufacture an extended range of star sensor assemblies to accommodate a wide range of pipe line sizes.

What is claimed is:

1. A flow meter for measuring the flow through a fluid-conveying pipeline whereby a meter installation adapter is provided fitted upstream of the flow meter in a pipeline, the pipeline defining several flanges, the flow meter being positioned in use downstream of one of the pipeline flanges, wherein the adapter comprises a tubular extension having an outside diameter size to enable its insertion into the pipeline upstream of the other of the pipeline flanges, said tubular extension has a downstream end configured to engage the flow meter such that a passageway defined by the tubular extension is located in a predetermined orientation relative to the flow meter, and wherein the inside diameter of the tubular extension is essentially the same as the inside diameter of the flow meter.

2. The flow meter according to claim 1, wherein the tubular extension is mounted on said adapter flange which in use is inserted between the flow meter flange and the other of the pipeline flanges.

3. The flow meter according to claim 1, wherein the flow meter and adapter flanges are configured such that the flow meter may be slipped sideways onto said adapter flange in one orientation only and co-operating surfaces on the flow meter and adapter flanges limit the movement of the flow meter flange relative to said adapter flange beyond the point at which the axes of the adapter and flow meter are aligned.

4. The flow meter according to claim 3, wherein the flow meter and adapter flanges define projections which determine the relative positions of said adapter and the flow meter.

5. The flow meter according to claim 2, wherein the flow meter flange defines a recess which receives an O-ring to form a seal between said adapter and the flow meter flanges.

6. The flow meter according to claim 1, wherein a sensor array is provided positioned in a passageway through which the fluid flow is to be monitored, comprising a unitary support extending from one wall of said passageway and extending at least partially in an area having a predetermined distance to a central portion of said passageway, and at least three flow sensors mounted on said unitary support in a non-linear array.

7. The flow meter according to claim 6, wherein said unitary support extends at least partially around the central portion of said passageway.

8. The flow meter according to claim 6, wherein said unitary support has a star-like design.

9. The flow meter according to claim 6, wherein said unitary support extends to a central position within said passageway and includes an at least partially annular portion supporting a series of sensors at substantially equal distances from the central position.

10. The flow meter according to claim 9, wherein said annular section supports four sensors spaced at equal intervals around the central position.

11. The flow meter according to claim 6, wherein each of the sensors is a thermal loss sensor.

* * * * *